United States Patent [19]
Barbour et al.

[11] Patent Number: 5,244,814
[45] Date of Patent: Sep. 14, 1993

[54] DECAY DETECTION IN WOOD

[75] Inventors: R. James Barbour, Russell; Ludmila L. Danylewych-May, North York; Roger Sutcliffe, Nepean, all of Canada

[73] Assignee: Forintek Canada Corporation, Vancouver, Canada

[21] Appl. No.: 703,116

[22] Filed: May 20, 1991

[51] Int. Cl.$^5$ .............................................. E01N 33/46
[52] U.S. Cl. ...................................... 436/173; 436/63; 436/153; 422/68.1; 422/78; 422/80; 422/82.02; 250/282; 250/287; 250/288
[58] Field of Search ............... 436/20, 63, 133, 173; 250/287, 282, 288; 422/68.1, 80, 82.02

[56] References Cited

U.S. PATENT DOCUMENTS

| | | | |
|---|---|---|---|
| 3,521,483 | 7/1970 | Millar et al. | 73/67.5 |
| 3,531,983 | 10/1970 | Heath et al. | 73/67.2 |
| 3,864,627 | 2/1975 | Shigo | 324/65 P |
| 3,877,294 | 4/1975 | Shaw | 73/67.2 |
| 4,482,250 | 11/1984 | Hirvonen et al. | 356/369 |
| 4,797,554 | 1/1989 | Blanchard et al. | 250/287 |
| 4,820,920 | 4/1989 | Bather | 250/282 |

OTHER PUBLICATIONS

Obst, John R.; "Analytical Pyrolysis of Hardwood and Softwood Digmis and It's Use in Lignin-Type Determination of Hardwood Vessel Elements". J. of Wood Chemistry and Tech. 3(4), pp. 377–397 (1983).

Panstin, A. J. and Zeeuw, Carl de; Textbook of Wood Technology, Third edition, published by McGraw-Hill, pp. 419–421.

*Primary Examiner*—James C. Housel
*Assistant Examiner*—Daniel Redding
*Attorney, Agent, or Firm*—Fetherstonhaugh & Company

[57] ABSTRACT

The presence of decay is determined in wood by testing a sample. The wood tested may be standing timber, cut timber or when coated in building structures. The testing occurs in very short time intervals so that tests can be carried out on timber in mills and the like. The method of testing includes heating a portion of a wood sample at a temperature in the range of about 220° to 350° C. to evaporate analytes from the wood, conveying the analytes in a sample gas flow into an ionizing chamber of an ion mobility spectrometer detector, ionizing the analytes within the ionizing chamber at a temperature in the range of about 220° to 350° C., generating an ion drift time signature in the detector, and comparing the signature with predetermined signatures representing decay in wood.

20 Claims, 18 Drawing Sheets

DECAY DETECTION IN WOOD

TECHNICAL FIELD

The present invention relates to sampling wood and determining if decay is present. More specifically, the present invention can determine the species of a wood sample and determine if decay is present in the sample.

BACKGROUND ART

Decayed wood is often not initially visible on the wood surface. For instance in the case of utility poles, decay often occurs in the portion of the pole below the ground. This makes it difficult to determine visually whether decay is present in the wood, particularly when decay generally occurs in the heartwood at the center of the pole and cannot be determined from the outside without drilling a hole into the wood. In present day examination of utility poles, it is normal to drill a hole downwards from above the ground line into the center of the wood so that a sample of the wood from the heart or core is extracted. In some cases decay is visible, however if the decay is incipient, then it is difficult to detect.

Vibration techniques have been suggested for determining decay in poles Shaw in U.S. Pat. No. 3,877,294 disclosed a vibration technique. Heath et al U.S. Pat. No. 3,531,983 related to Sonic testing. Miller et al in U.S. Pat. No. 3,521,483 and Shigo in U.S. Pat. No. 3,864,627 utilize electrical signals to detect the presence of decay.

There is also a need to determine if decay is present in standing trees, logs, and lumber being processed in sawmills, pulpmills or other manufacturing plants, as well as wood in use. Decay is often not visible from the exterior of trees, boards, or other wood products. Detection of decay in these situations would allow manufacturers to select the highest value processing option for individual pieces. In the case of wood in use, decay detection would allow engineers, or others responsible for the maintenance of structures, to determine when and if remedial steps are necessary. Some indication of the severity of decay or residual strength of the wood member would also be useful.

In copending application Ser. No. 444,878 filed Dec. 4, 1989, now U.S. Pat. No. 5,071,771 is disclosed a method of producing an ion mobility signature representing a wood sample and then comparing the signature with known signatures of wood species to determine the species of the sample. There is a need to determine not only the species but also to detect decay in a log or board at the same time that the species is determined. The time that is available for detecting decay at a sawmill is about one half to ten seconds per sample.

DISCLOSURE OF INVENTION

It is an aim of the present invention to detect decay in wood products or detect fungi in other natural products by utilizing an ion mobility spectrometer, and conduct the tests in a short time generally within ten seconds. It is a further aim to combine identification of species of a wood sample that has little or no decay present, or to identify decay present in a wood sample.

A further aim of the present invention is to detect incipient decay in sapwood or heartwood of a log, cut lumber, standing structure or tree regardless of moisture content of the wood, and regardless of external conditions, namely temperature and humidity.

A still further aim of the present invention is to use ion mobility spectrometry to determine the stage to which decay has progressed in wood, and to determine if the wood is suitable for its intended use based on the severity of decay present.

By producing an ion mobility signature for a wood sample having decay therein, one is able to determine certain peaks in the signature representing chemicals resulting from the decayed wood or fungi present in the wood. At the same time by knowing the species of wood being tested, one can compare a sample of a particular species without decay and one that has decay therein. The peaks representing decay are clearly visible and by comparing IMS signatures from samples of known wood species with and without decay, one is able to detect whether decay is present in a wood sample. One cannot necessarily detect the wood species in a sample having extensive decay therein, but one can detect the severity of the decay depending on the number, position and intensity of the peaks representing decay.

The present invention provides a method of determining the presence of decay in wood, comprising the steps of: heating a portion of a wood sample at a temperature in the range of about 220° to 350° C. to evaporate analytes from the wood sample, conveying the trace analytes in a sample gas flow into an ionizing chamber of an ion mobility spectrometer detector, ionizing the analytes within the ionizing chamber at a temperature in the range of about 220° to 350° C., generating an ion drift time signature in the detector, and comparing the signature with predetermined signatures representing decay in wood.

In another embodiment of the present invention there is provided an apparatus for determining presence of decay in wood, comprising means for heating at least a portion of a wood sample at a temperature in the range of about 220° to 350° C. to evaporate analytes from the wood sample, an ion mobility spectrometer detector adapted to generate an ion drift time signature from the analytes admitted into an ionizing chamber of the detector, the chamber having a temperature in the range of about 220° to 350° C., and comparison means to compare peak patterns on the ion drift time signature with known peak patterns representing decay in wood.

BRIEF DESCRIPTION OF DRAWINGS

In drawings which illustrate embodiments of the present invention.

BEST MODES FOR CARRYING OUT THE INVENTION

Figure 1:
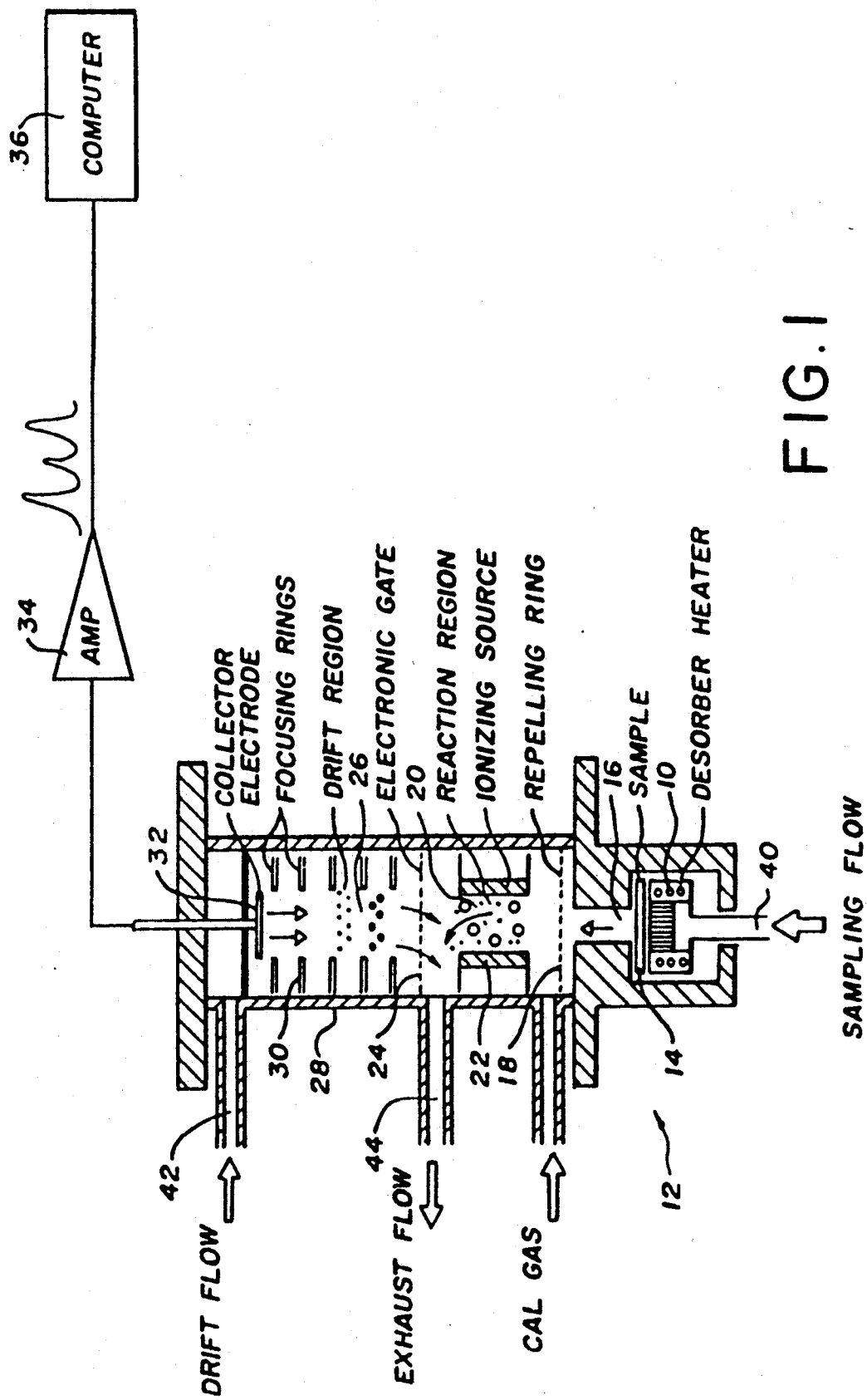
FIG. 1 is a schematic diagram showing an ion mobility spectrometer suitable for analyzing a wood sample according to the present invention.

An ion mobility spectrometer (IMS) detector 12 is illustrated in FIG. 1. A desorber heater 10 is positioned at one end of the detector 12 and a wood sample 14 rests on top of the filter above the desorber heater 10. A passage 16 from the desorber heater 10 leads through a repelling ring 18 to an ionizing chamber 20 which includes a weak radioactive source. An electronic gate 24 separates the ionizing chamber 20 from a drift region 26. The drift region 26 is a drift tube 28 with a series of stacked cylindrical metal rings 30 to produce a uniform electric field throughout the drift region 26. An ion 32 passes an electric current through an amplifier 34 into a computer 36 where the signal is averaged and an ion drift time signature is produced. This ion drift time signature is then compared with a programmed time signature representing different species of wood, or different stages of decay in the wood, and sample identification then takes place. The ion drift time signature can be displayed in real time and stored in the computer 36 for permanent records from which a hard copy can be obtained.

A sampling gas flow 40 entrains analytes from the heated wood sample 14, and conveys the analytes through a transfer line 16 into the ionizing chamber 20 of the detector. The transfer line 16 containing the analytes is maintained at a high temperature to prevent condensation of the analytes. The drift region 26 and the ionizing chamber 20 are at atmospheric pressure. The ionizing source in one embodiment is $^{63}$Ni, a radioactive isotope emitting beta particles. These beta particles collide with oxygen and nitrogen molecules in the sampling gas flow 40 forming both positive and negative ions. These ions undergo fast ion molecule reactions with reactant molecules. The reactant ions ionize the analytes introduced into the sampling gas flow. As a result of complex ion molecule reactions that take place in the ionizing chamber 20, the molecules of some analytes form stable ions while others do not. These ions are prevented from entering the drift region 26 by the electronic gate 24 and cannot return to the passageway 16 because of the repelling ring 18. When the gate 24 is open, the ions accelerate under the influence of a strong electric field through the drift region 26 towards the collector 32. The gate 24 is repetitively opened at brief intervals (typically 0.2 milliseconds) emitting pulses of mixed ions into the drift region 26. A typical time between pulses is 20 milliseconds. As the ions drift against the counter current drift gas flow, the ions in any particular pulse separate into their individual chemical species based upon their differing intrinsic properties. The arrival of the individual ion pulses at the collector 32 produces a characteristic ion arrival time spectrum. This ionic signal in the form of a weak electric current from the collector 32 is amplified by the amplifier 34 and then fed to a computer 36 where it is filtered, digitized and stacked to increase signal to noise ratio. The number of sweeps or cycles can be varied and an average signal generated or stored. This average signal can be viewed on a computer monitor or in real time on an appropriate display. Because each ion travels at different velocities, the ions are separated in drift time as they arrive at the collector 32. A plot of ion intensity as a function of drift time is referred to as a plasmagram or signature.

A drift gas flow 42 was maintained in the drift region 26 against the ion travel direction and exited at an exhaust 44 together with the sampling gas 40. A typical time between pulses is 20 milliseconds, this represents an analysis time for one pulse of the gate 24.

The wood sample is obtained in a number of different ways either by taking out a small wood sample with a drill or core borer or removing a vapor sample through a heated hollow needle. In the case of cut lumber, the sample may be taken internally or from the surface, or alternatively a portion of the lumber heated, either by remote or contact methods, to evaporate an analyte, and the analyte drawn into the ionizing chamber of the analyzer. In the case of a utility pole, a core borer may be used to remove a plug, and a series of samples along the length of the plug may be analyzed to create a decay profile through the pole.

The sample or at least a part of the sample is heated to a temperature in the range of about 220° to 350° C. and the analyte conveyed to the ionizing chamber 20. The manner of producing the signature is similar to that shown in copending application Ser. No. 444,878. Temperature in the ionizing chamber is in the range of about 220° to 350° C. and the same polarity is provided in the zone to retain the same polarity ions for production of ionic signals and a subsequent drift time signatures that enable wood species to be determined, and decay to be detected. For each detection at least a portion of the wood sample is heated to within the desired desorption temperature range, the analyte is carried to the ionizing chamber and a number of pulses occur in each detection cycle. The complete detection cycle occurs in less than a second preferably less than one half second from entry of the analytes into the ionizing chamber. For the tests to obtain the IMS signatures in the figures, each signature was taken in a time of about 0.3 to 4.5 seconds from commencement of heating the sample. In the tests conducted, a negative polarity was provided in the ionizing chamber 20 and the drift region 26, and the negative ions were measured for the drift time signatures.

Signatures were obtained for a number of different wood species having varying stages of decay in accordance with the method disclosed in copending application Ser. No. 444,878. The signatures indicate the drift time and the reduced mobility which is determined by referring the measured ion drift time to the drift time and reduced mobility of a calibrant ion. These are shown by a number of peak patterns which represents the analysis of the trace vapor.

Figure 2:
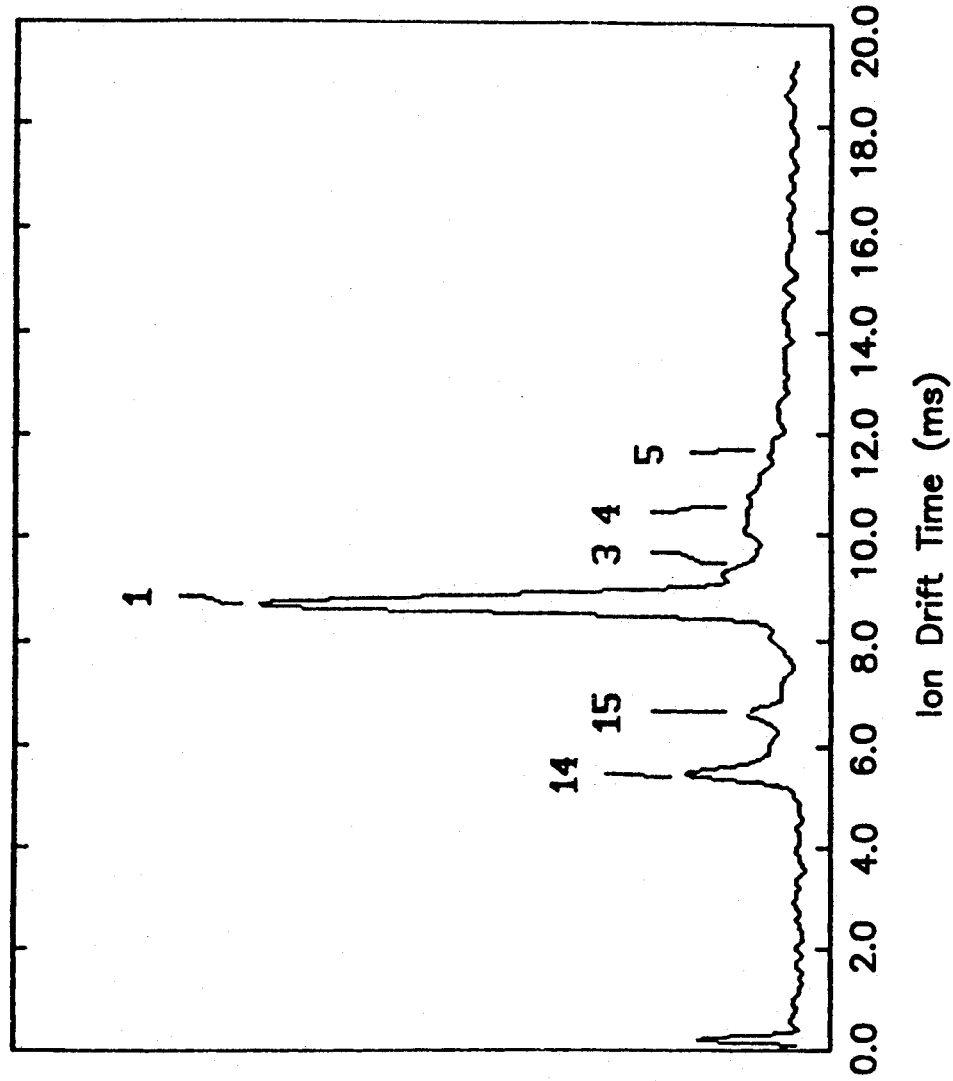
FIGS. 2 to 5 show ion mobility signatures for samples of balsam fir heartwood for sound, incipient decay, moderate decay and heavy decay.
Figure 3:
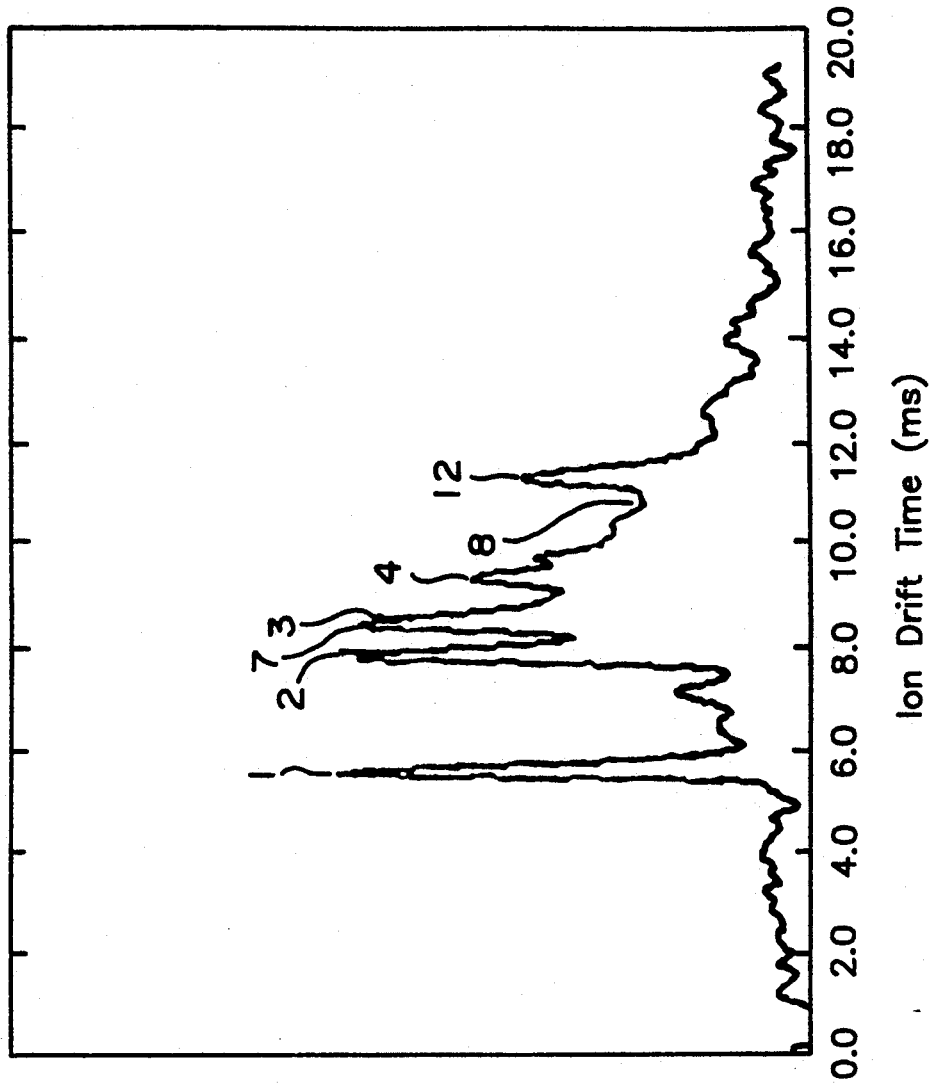
Figure 4:
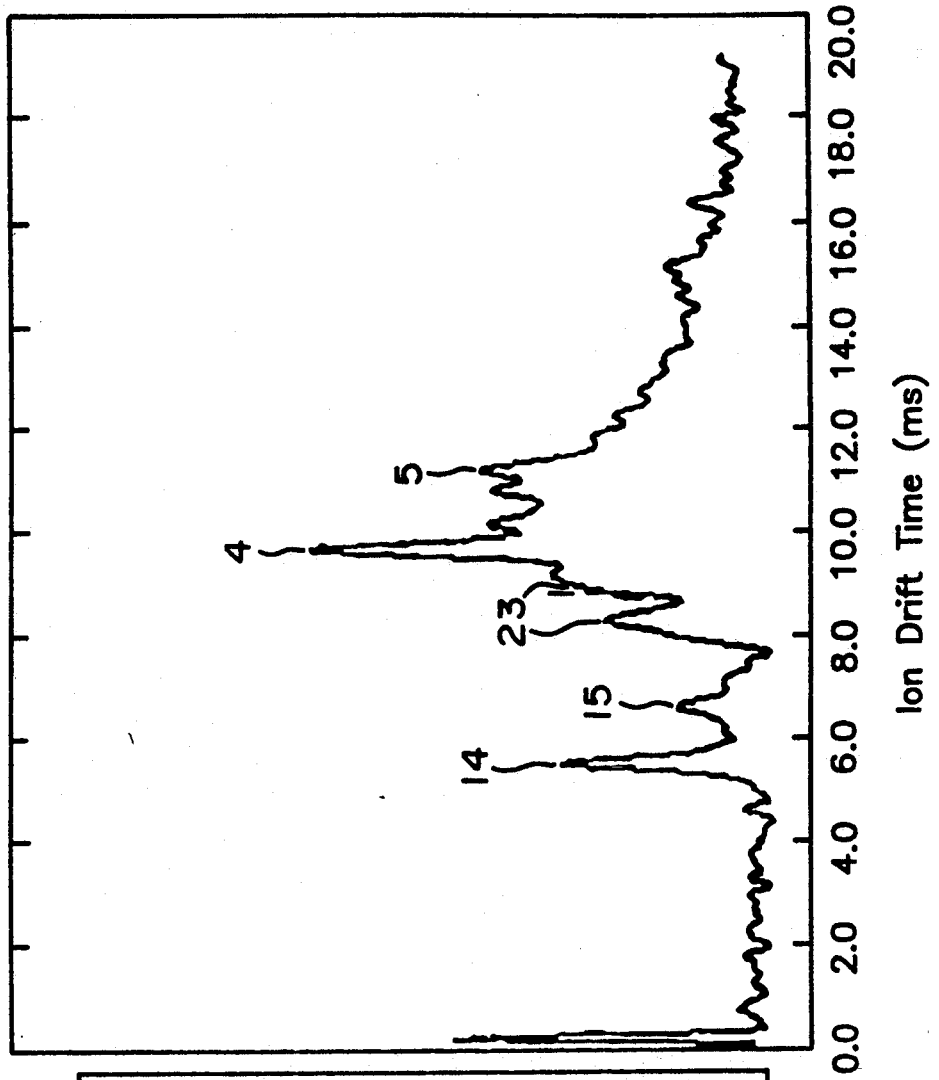
Figure 5:
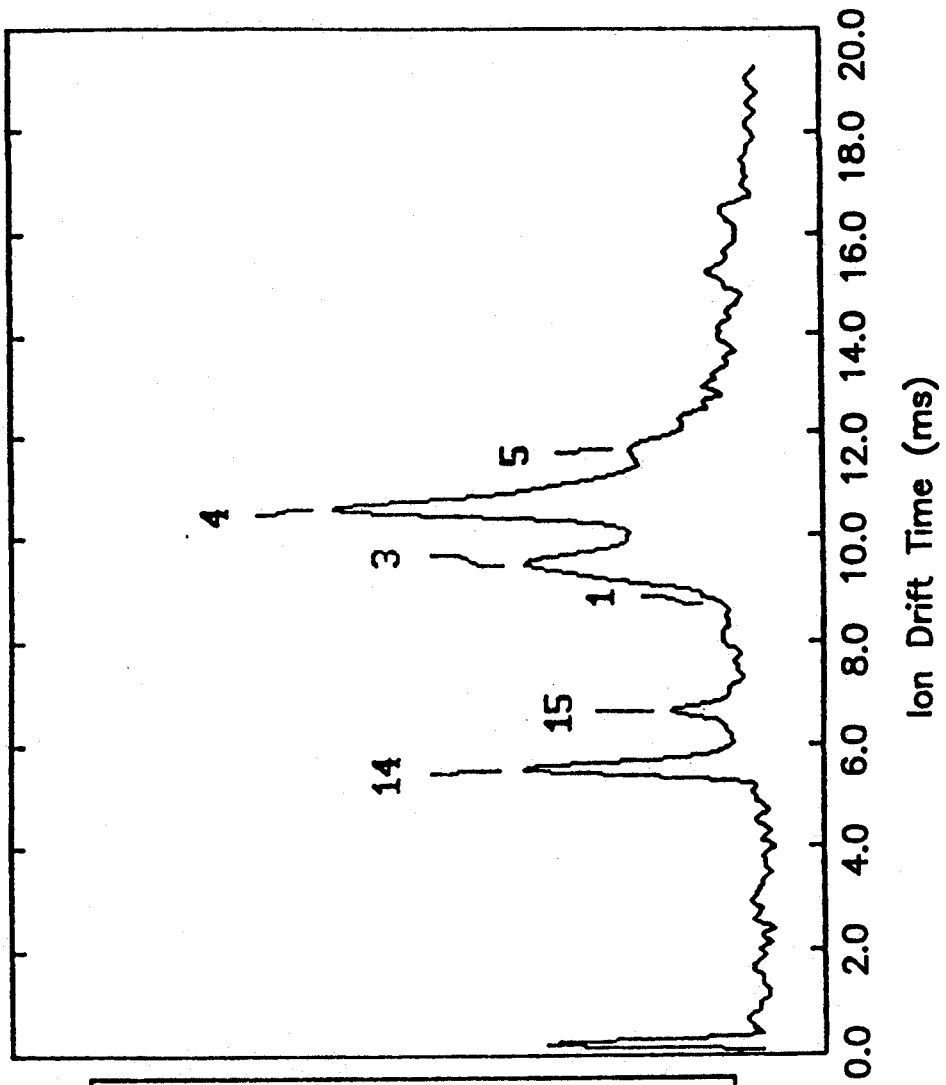

FIGS. 2 to 5 show the progression from sound to heavy decay for balsam fir heartwood. In FIG. 2 the sound sample, the only peak present is at reduced mobility of 1.847. The reduced mobilities referred to are all in $cm^2 V^{-1}S^{-1}$. This peak is used to identify the wood species. Incipient decay is shown in FIG. 3 and peaks with reduced mobility of 1.953, 1.807, 1.663 and 1.449 are now present. In FIG. 4 these same peaks are present, but the intensity of the species peak, reduced mobility of 1.847, is much lower. FIG. 4 is a sample of moderate decay, whereas FIG. 5, which is a heavy decay sample, shows a completely different set of peaks with reduced mobilities of 1.698, 1.521 and 1.371 representing decay. The species peak of 1.847 can no longer be seen.

Figure 6:
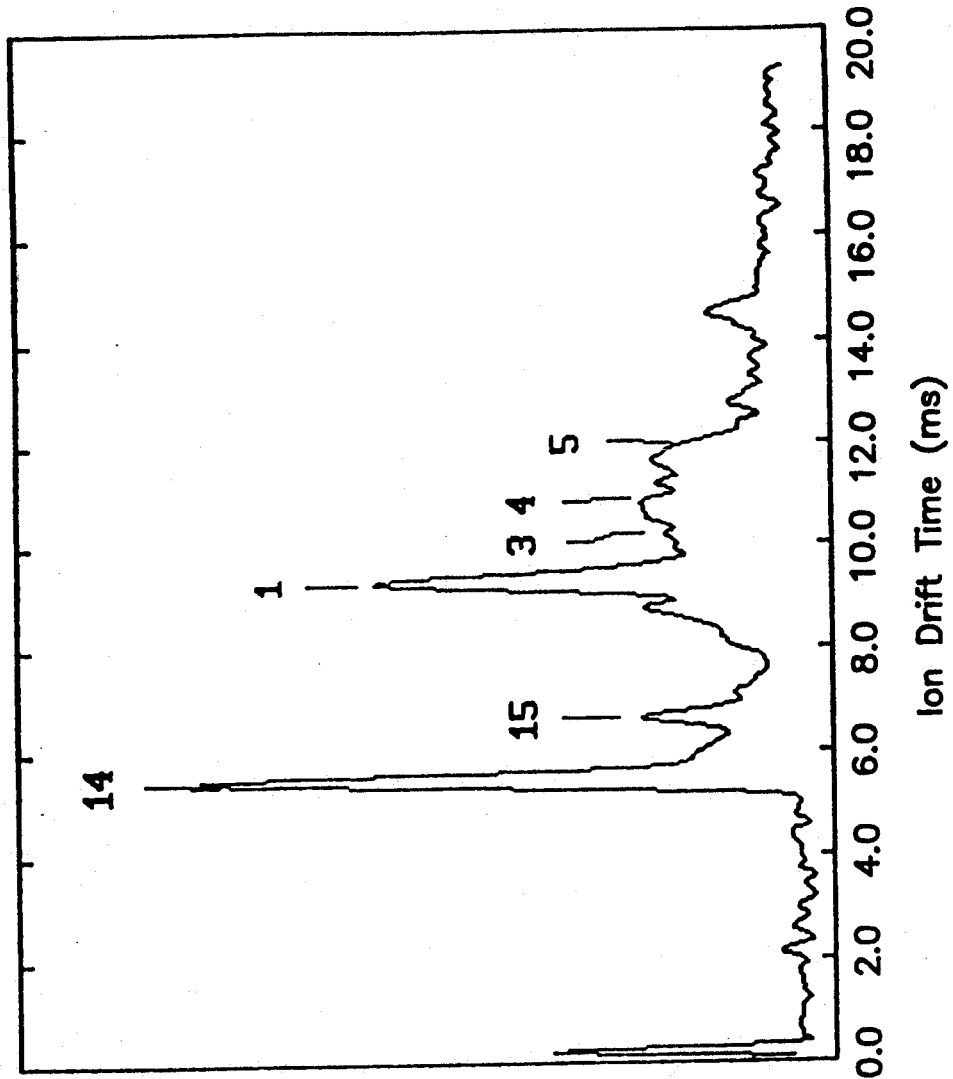
FIGS. 6 to 8 show ion mobility signatures for samples of spruce heartwood for sound, incipient decay and heavy decay.
Figure 7:
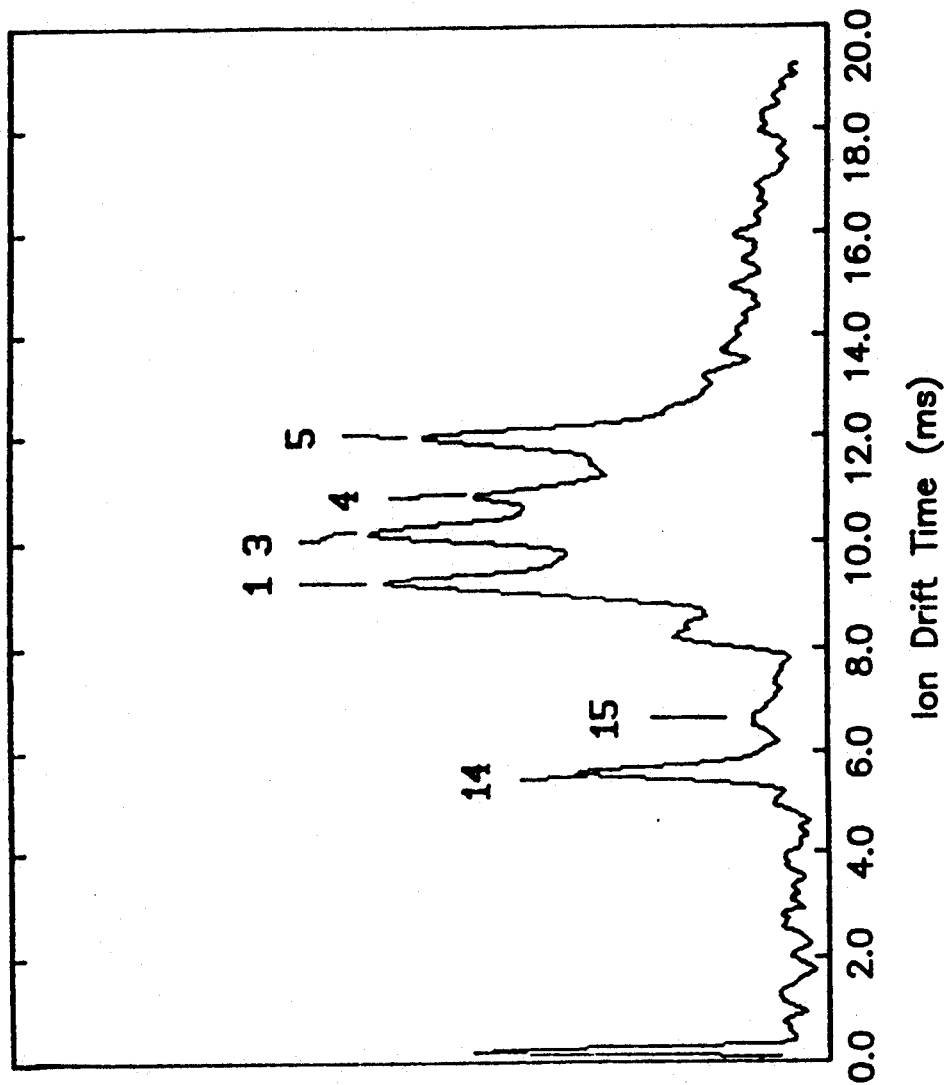
Figure 8:
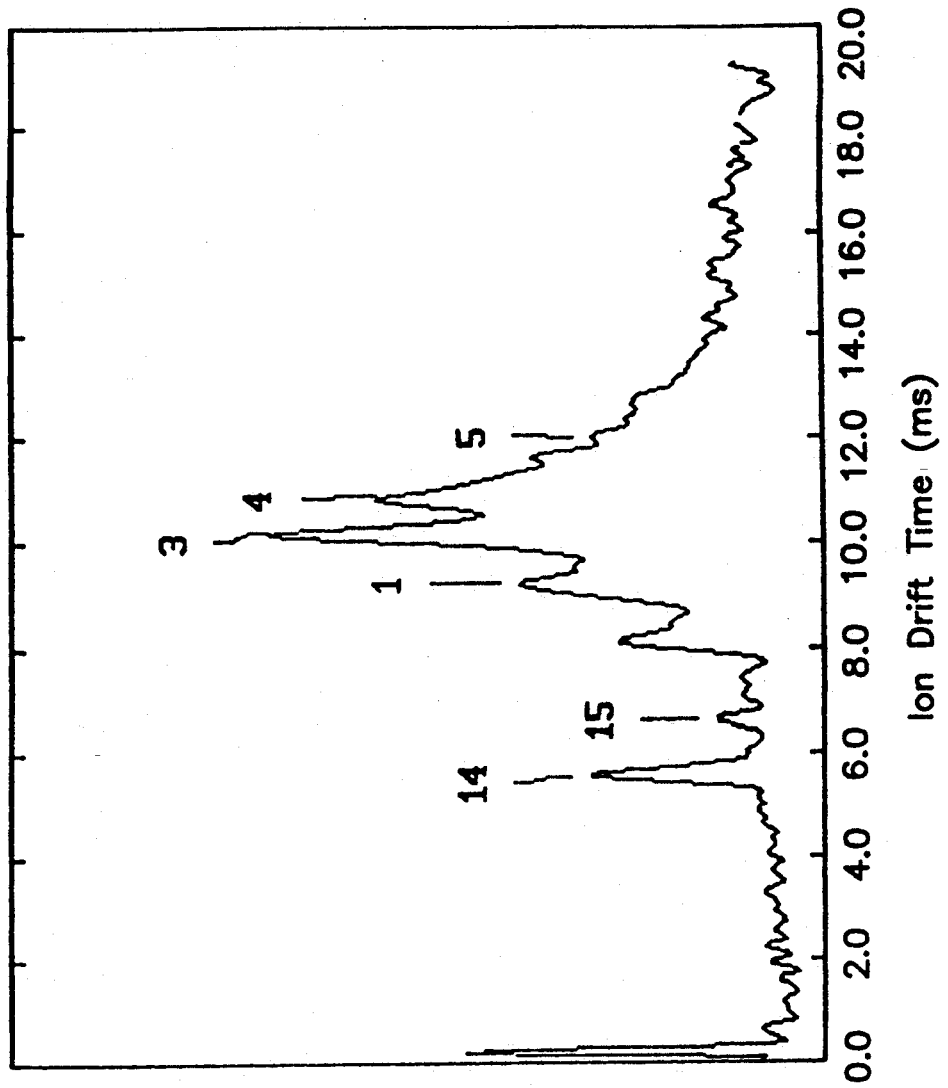

A similar pattern occurs for spruce heartwood in FIGS. 6, 7 and 8. As can be seen the relative intensity of the peaks with reduced mobilities representing species decrease whereas the relative intensities of the peaks representing decay change. In FIG. 7, the incipient decay sample, the peak with reduced mobility of 1.337, representing decay, is prominent but is almost undetectable in FIG. 8 when the decay was heavy.

Figure 9:
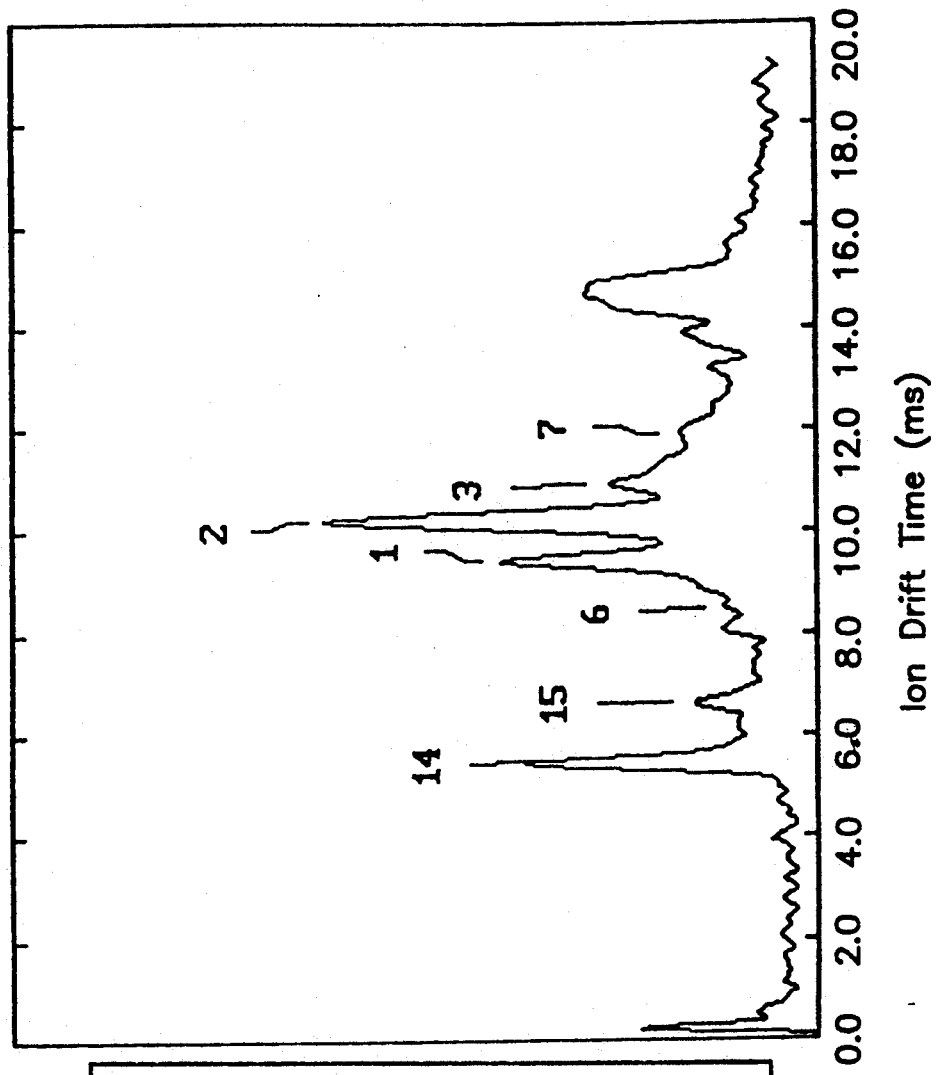
FIGS. 9 to 11 show ion mobility signatures for samples of douglas fir heartwood for sound, incipient decay and heavy decay.
Figure 10:
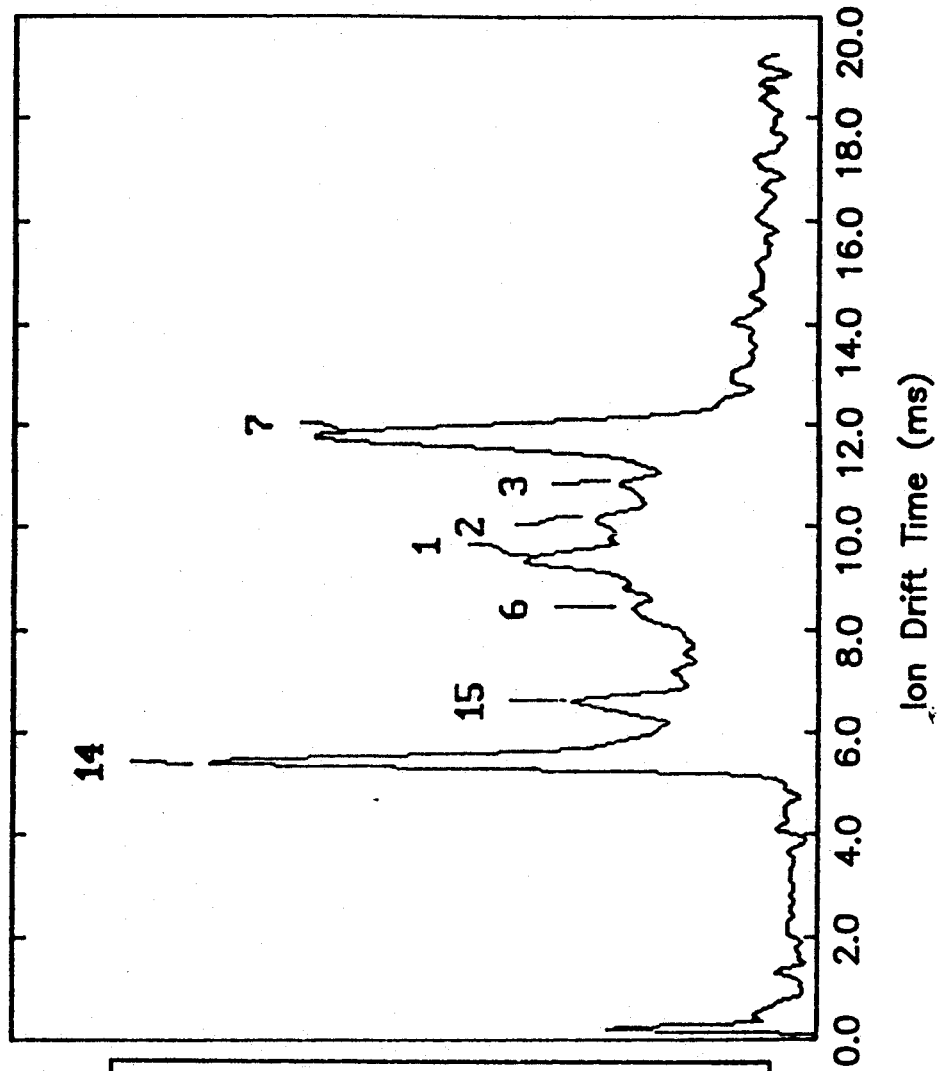
Figure 11:
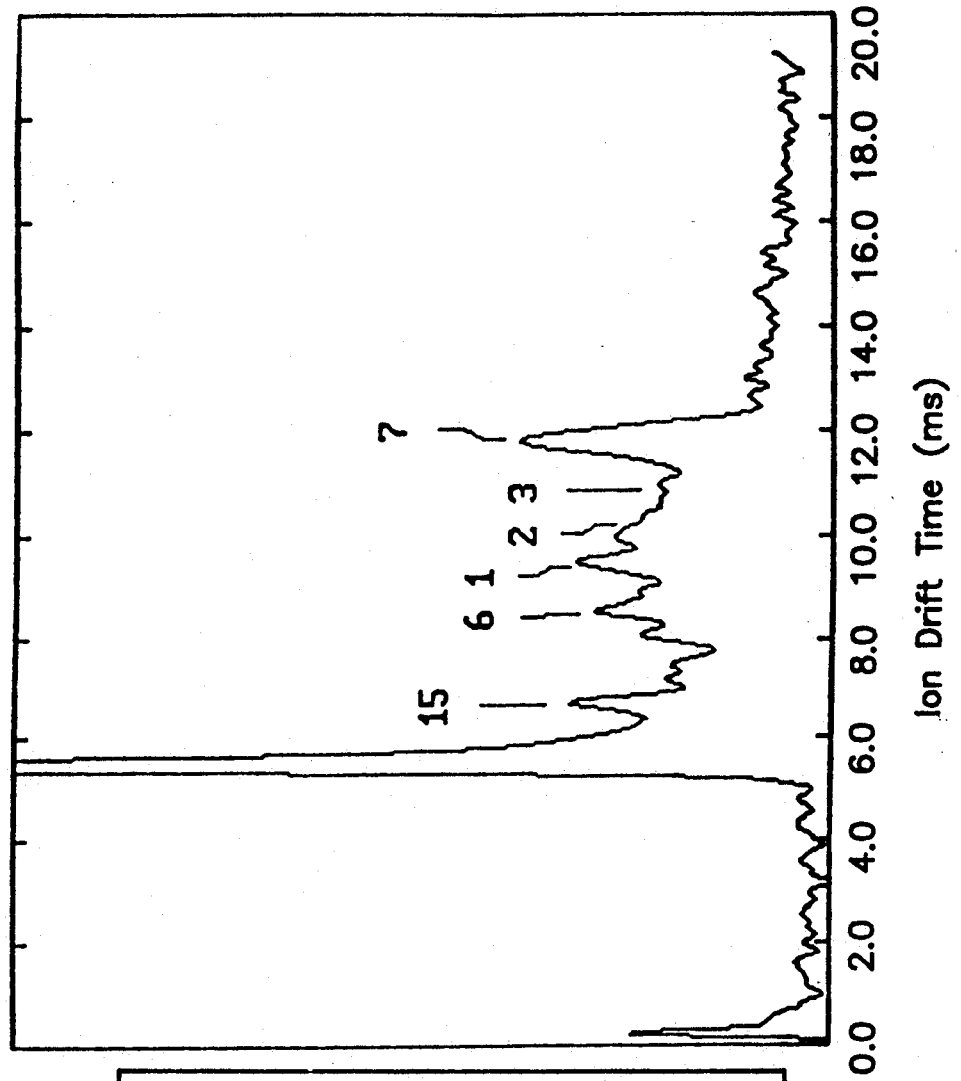

FIGS. 9, 10 and 11 show douglas fir heartwood and the pattern is repeated as the decay increases. The peaks with reduced mobilities of 1.700, 1.573 and 1.475 shown in FIG. 9 representing wood species decrease in FIG. 10 and almost disappear in FIG. 11, however the peaks representing decay change. The reduced mobility peak of 1.885 increases while the reduced mobility peak of 1.350 decreases from FIG. 10 to FIG. 11.

Figure 12:
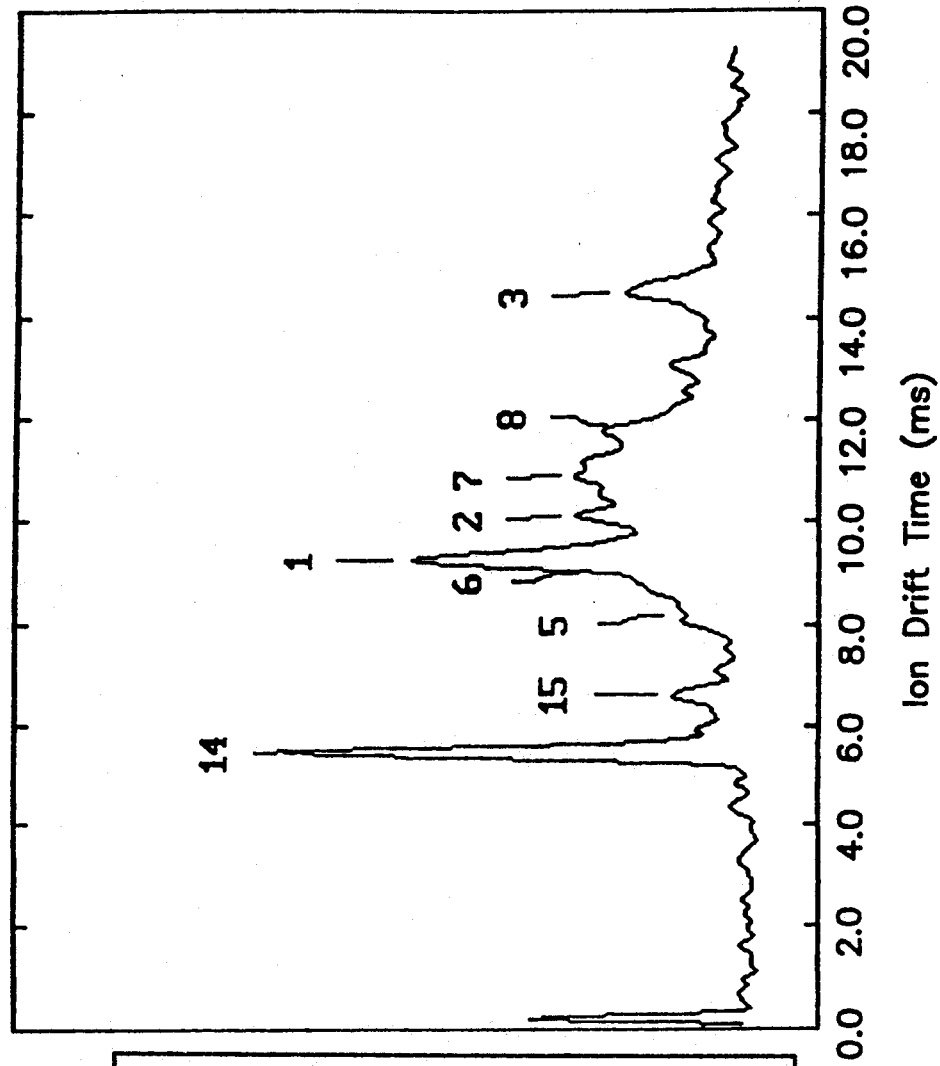
FIGS. 12 to 14 show ion mobility signatures for samples of red pine heartwood for sound, incipient decay and heavy decay.
Figure 13:
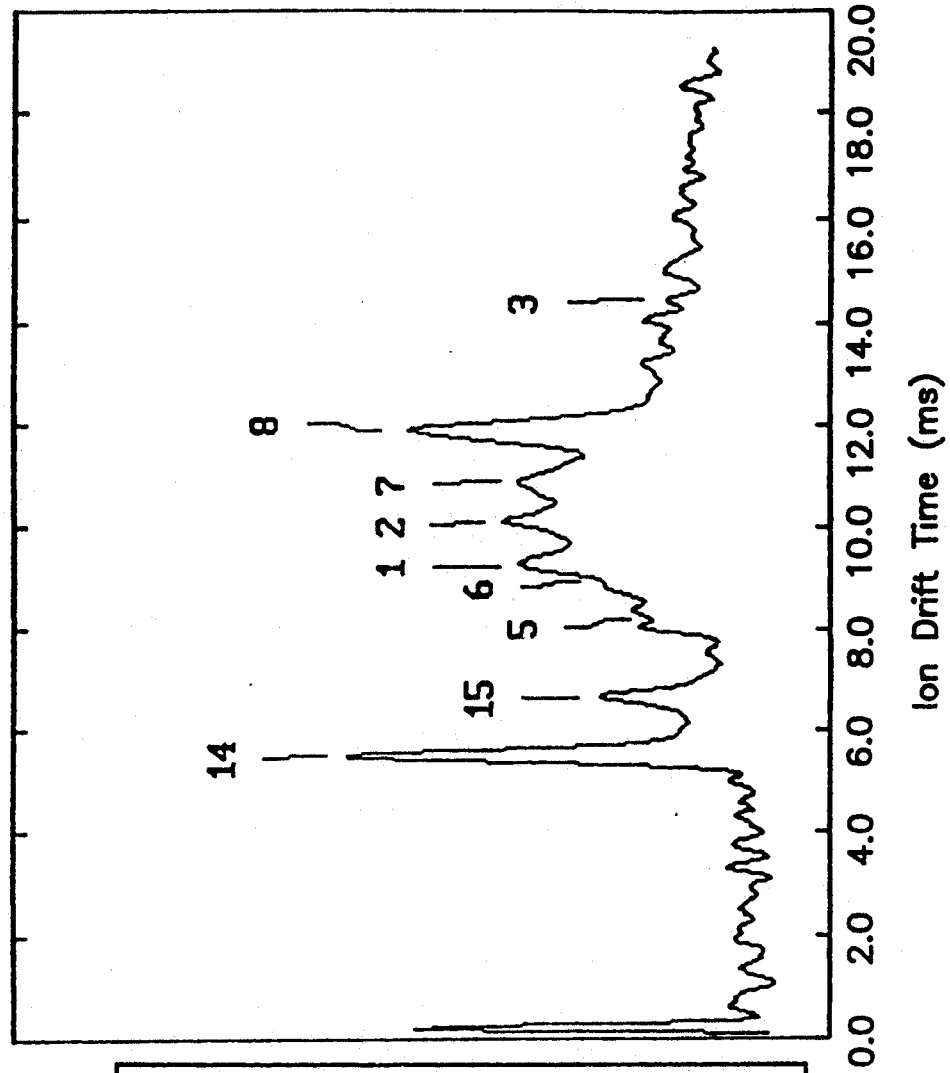
Figure 14:
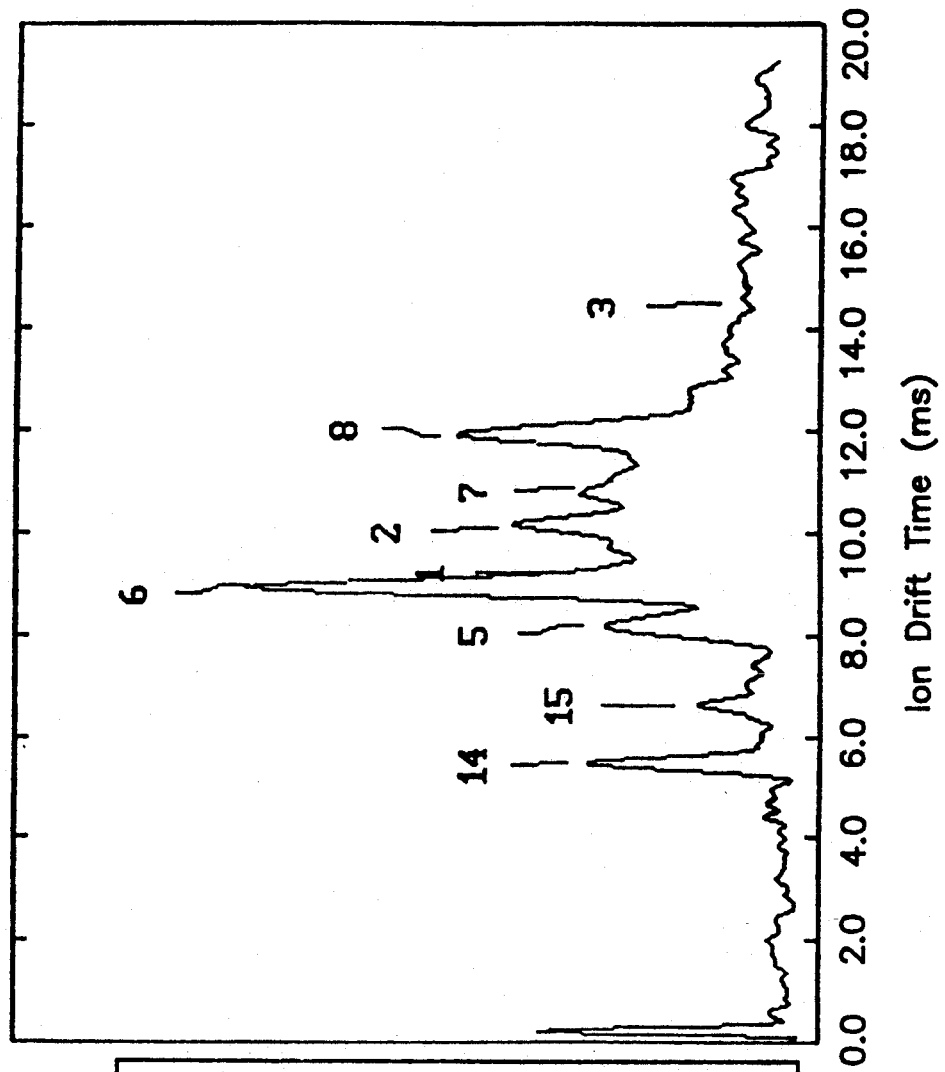
Figure 15:
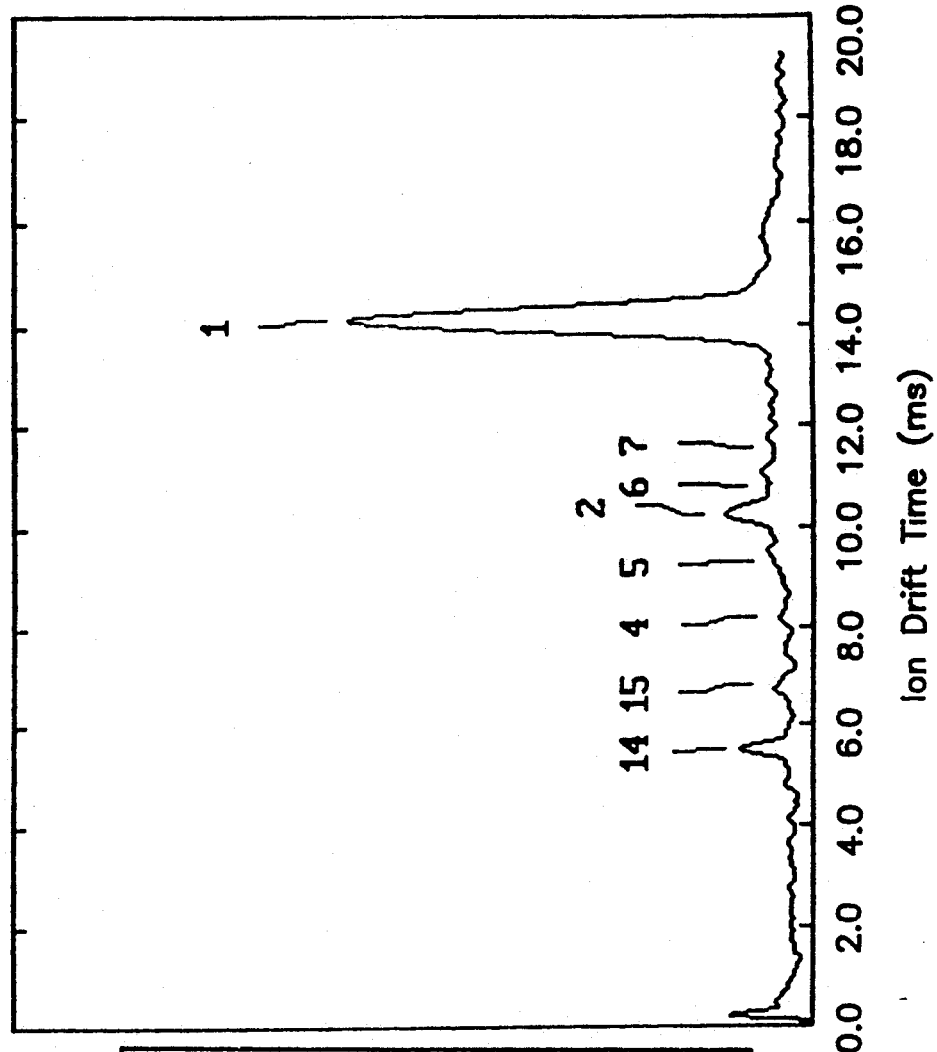
FIGS. 15 and 16 show ion mobility signatures for samples of jack pine heartwood for sound and heavy decay.
Figure 16:
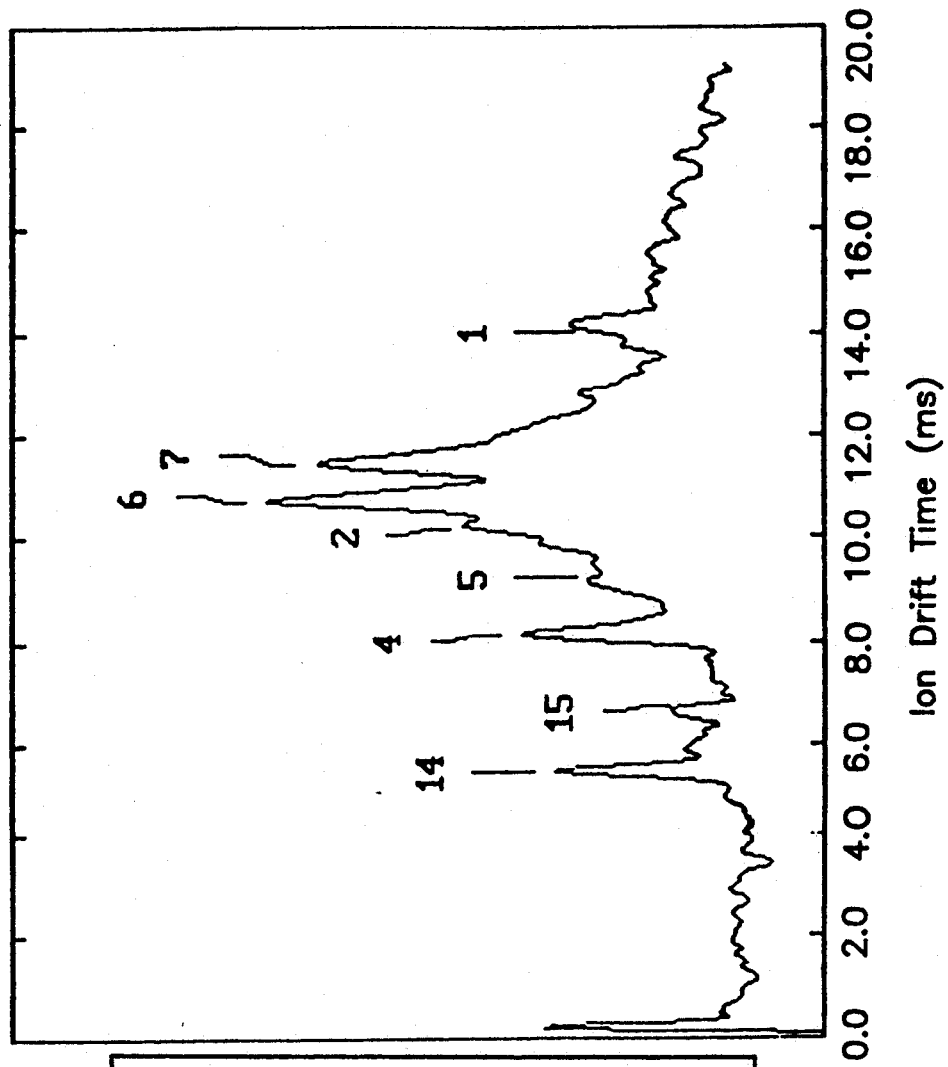
Figure 17:
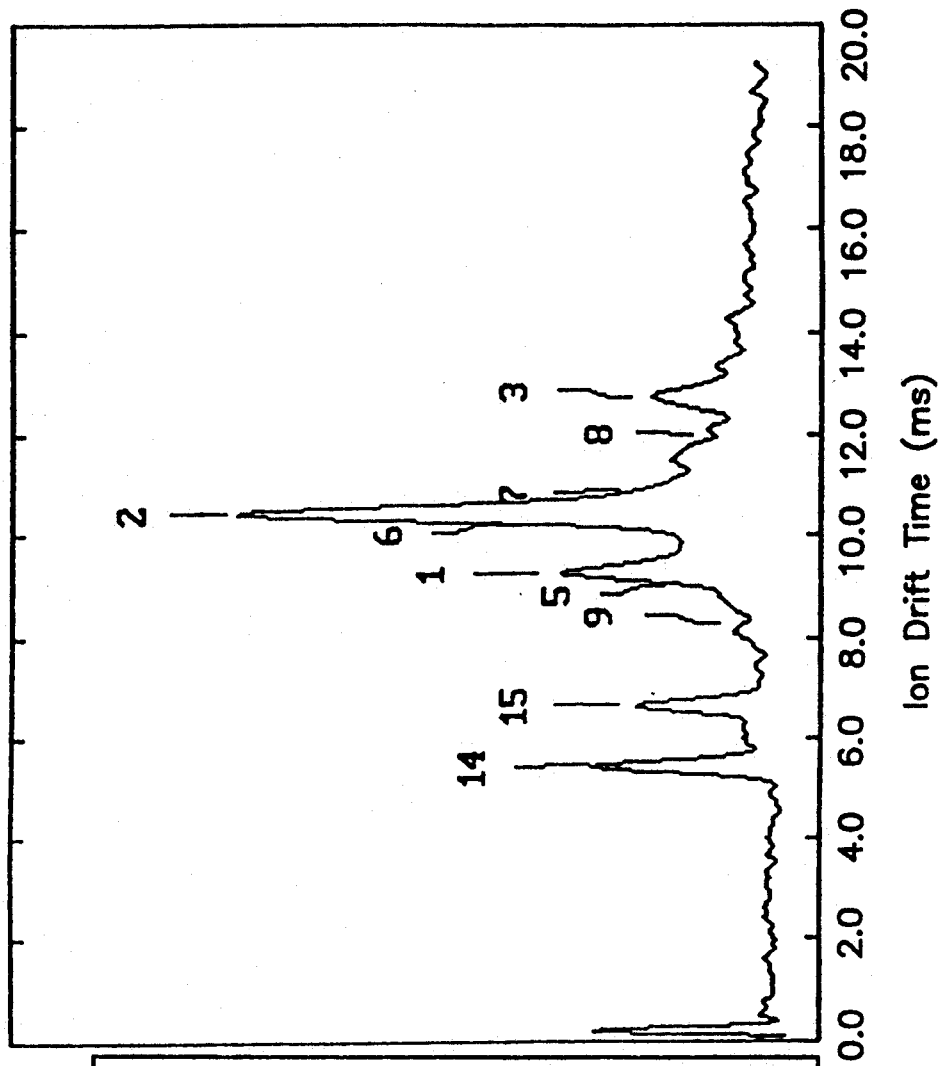
FIGS. 17 and 18 show ion mobility signatures for samples of western cedar heartwood for sound and heavy decay.
Figure 18:
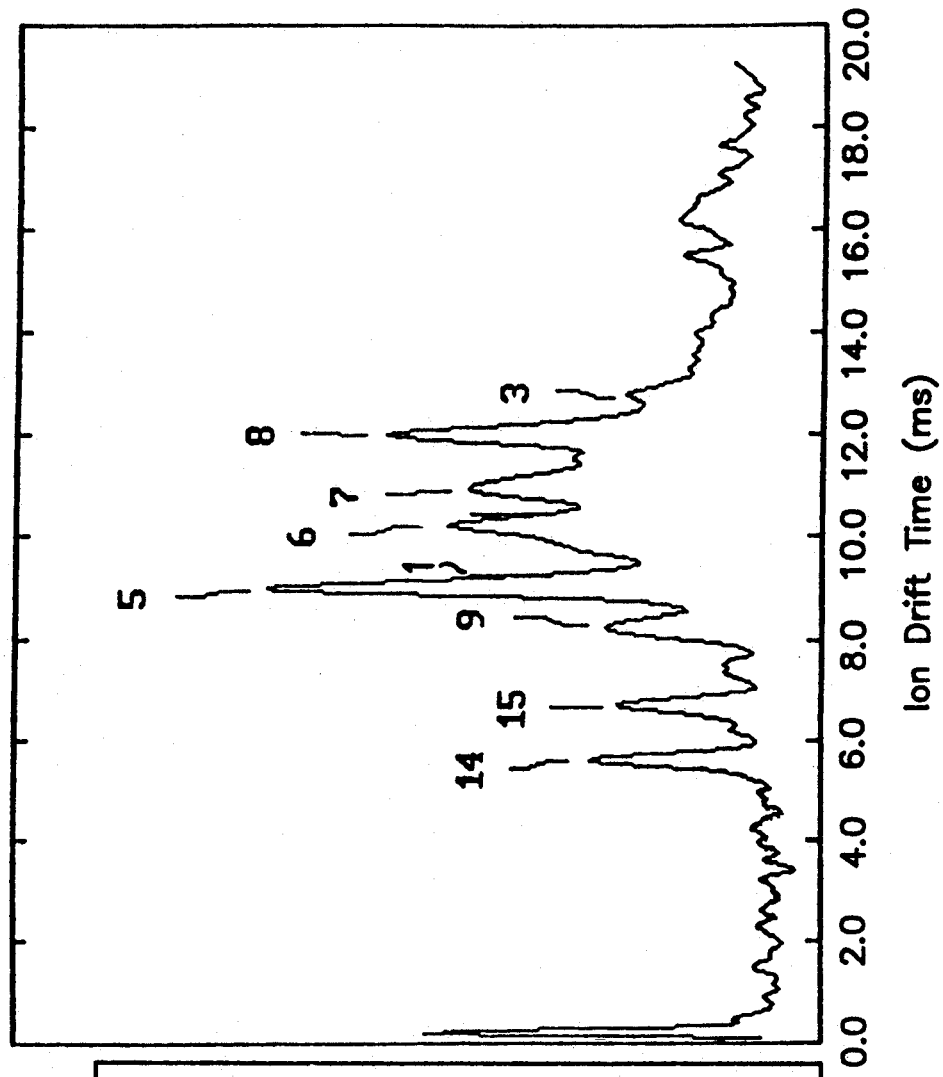

The red pine heartwood samples shown in FIGS. 12, 13 and 14 show decreases in the peaks representing species (1.737, 1.591 and 1.100) and the peaks representing decay tend to increase and change in relative intensity. The jack pine heartwood samples shown in FIGS. 15 and 16 and the western cedar heartwood samples shown in FIGS. 17 and 18 also follow the same pattern.

The peaks representing species decrease as the stages of decay increase. The peaks representing decay change as the levels of decay change. This is characteristic of the intensity of the deterioration. As the peaks which identify species disappear, it becomes more difficult to identify species. However, knowing that certain peaks represent decay, and comparing signatures with known signatures one can identify decay and even the level of decay in the wood.

In certain cases by comparing decayed wood signatures, one is able to identify the species of the decayed wood.

| REDUCED MOBILITY Ko $(cm^2V^{-1}s^{-1})$ | WOOD SPECIES | | | | | | |
|---|---|---|---|---|---|---|---|
| | SPRUCE | | JACK PINE | | BALSAM FIR | | |
| | SOUND | DECAYED | SOUND | DECAYED | SOUND | INCIPIENT DECAY | HEAVY DECAY |
| 2.002 | | | | XXXXXXXXX | | | |
| 1.959 | | | | | | | |
| 1.953 | | | | | | XXXXXXXXX | |
| 1.933 | | | | | | | |
| 1.885 | | | | | | | |
| 1.847 | | | | | XXXXXXXXX | | |
| 1.807 | | | | | | XXXXXXXXX | |
| 1.788 | | | | | | | |
| 1.765 | | | | XXXXXXXXX | | | |
| 1.737 | XXXXXXXXX | | | | | | |
| 1.700 | | | | | | | XXXXXXXXX |
| 1.663 | | | | | | XXXXXXXXX | |
| 1.601 | | | XXXXXXXXX | | | | |
| 1.591 | | | | | | | |
| 1.573 | | XXXXXXXXX | | | | | |
| 1.537 | | | | | | | |
| 1.520 | | | | XXXXXXXXX | | | XXXXXXXXX |
| 1.475 | | XXXXXXXXX | | | | | |
| 1.449 | | | | | | XXXXXXXXX | |
| 1.421 | | | | XXXXXXXXX | | | |
| 1.371 | | | | | | | XXXXXXXXX |
| 1.350 | | | | | | | |
| 1.337 | | XXXXXXXXX | | | | | |
| 1.265 | | | | | | | |
| 1.160 | | | | XXXXXXXXX | | | |
| 1.108 | | | | | | | |

| REDUCED MOBILITY Ko $(cm^2V^{-1}s^{-1})$ | DOUGLAS FIR | | RED PINE | | W. RED CEDAR | |
|---|---|---|---|---|---|---|
| | SOUND | DECAYED | SOUND | DECAYED | SOUND | DECAYED |
| 2.002 | | | | | | |
| 1.959 | | | | XXXXXXXXX | | |
| 1.953 | | | | | | |
| 1.933 | | | | | | XXXXXXXXX |
| 1.885 | | XXXXXXXXX | | | | |
| 1.847 | | | | | | |
| 1.807 | | | | | | |
| 1.788 | | | | XXXXXXXXX | | XXXXXXXXX |
| 1.765 | | | | | | |
| 1.737 | | | XXXXXXXXX | | XXXXXXXXX | |
| 1.700 | XXXXXXXXX | | | | | |
| 1.663 | | | | | | |
| 1.601 | | | | | | |
| 1.591 | | | XXXXXXXXX | | | |
| 1.573 | XXXXXXXXX | | | | | XXXXXXXXX |
| 1.537 | | | | XXXXXXXXX | | |
| 1.520 | | | | | | |
| 1.475 | XXXXXXXXX | | | XXXXXXXXX | | XXXXXXXXX |
| 1.449 | | | | | | |
| 1.421 | | | | | | |
| 1.371 | | | | | | |
| 1.350 | | XXXXXXXXX | | XXXXXXXXX | | |
| 1.337 | | | | | | XXXXXXXXX |

| WOOD SPECIES | | |
|---|---|---|
| 1.265 | | XXXXXXXXX |
| 1.160 | | |
| 1.108 | XXXXXXXXX | |

The table summarizes results from FIGS. 2 to 18 showing reduced mobilities for ions representing sound and decayed wood for different species.

It has been found that moisture in the wood has little effect on the signatures. For the specific tests carried out to produce the signatures shown in FIGS. 2 to 18 desorption temperature was 300° C. The ionizing temperature was 260° C.

Comparison of the signatures produced by testing standing timber or cut timber may be compared manually by checking the peak patterns representing the wood sample. Alternatively the signatures may be computerized for comparing the peaks with those of known signatures for specific wood species and decay in those species. The sampling of the analyte is preferably carried out in the range of about 0.3 to 5 seconds. The time of 0.5 to 2 seconds is all that is needed for desorbing the wood sample, even in severe cold, thus this permits wood samples to be desorbed on cut timber moving in a sawmill. Determining species and presence of decay in timber is determined within a short time from the initial sample being desorbed.

Whereas the tests described herein have all referred to heartwood of different wood species, the method of detecting decay is not limited to heartwood but can apply to sapwood and other lignocellulosic materials. Initially tests are run to produce IMS signatures of different types of material that have decay therein. Comparisons may then be made with tests on samples to compare signatures with known signatures. From this information a determination of species and/or decay may be made.

Tests to determine the presence of decay may be carried out on all lignocellulosic materials, for instance standing structures such as buildings, which have wood or beams that are coated with paint, stain or other types of coating. A wood sample must be taken from under the coating. The sample may be sapwood or heartwood, but the presence of decay can be determined and in some cases when decay is not at an advanced stage, the species of the wood determined. In the case where there is advanced decay, and the wood species cannot be identified, another sample of structurally sound wood with little or no decay present should be tested in order to identify wood species.

Railway ties and utility poles can also be tested but the sample should be taken beneath the weathered surface. If a preservative or other chemical is present in high concentrations, the signature will not allow one to determine if decay is present, or the sample wood species. However in most cases, and particularly when decay is present, the concentration of the preservative is such that it does not effect detection of the decay.

Various changes may be made to the embodiments shown herein without departing from the scope of the present invention which is limited only by the following claims.

The embodiments of the present invention in which an exclusive property of privilege is claimed are defined as follows:

1. A method of determining the presence of decay in a known species of wood, comprising the steps of:
   heating a portion of a wood sample at a temperature in the range of about 220° to 350° C. to evaporate analyte from the wood sample,
   conveying the analyte in a sample gas flow into an ionizing chamber of an ion mobility spectrometer detector,
   ionizing the analytes within the ionizing chamber at a temperature in the range of about 220° to 350° C.,
   generating an ion drift time signature of the sample in the detector, and
   comparing the signature of the sample with predetermined signatures representing decay in said known species of wood, to determine presence of decay in the wood sample.

2. A method of determining the presence of decay in a known species of wood, comprising the steps of:
   heating a portion of a wood sample at a temperature in the range of about 220° to 350° C. to evaporate analytes from the wood sample,
   conveying the analytes in a sample gas flow into an ionizing chamber of an ion mobility spectrometer detector,
   generating an ion drift time signature in the detector wherein the analytes are ionized in the ionizing chamber at a temperature in the range of about 220° to 350° C. maintained in the chamber, and
   comparing peak patterns on the ion drift time signature of the sample with known peak patterns representing decay in said known species of wood, to determine presence of decay in the wood sample.

3. The method of determining the presence of decay in wood according to claim 1 wherein a negative polarity is maintained in the ion mobility spectrometer detector.

4. The method of determining the presence of decay in wood according to claim 1 wherein the wood sample is taken from standing timber.

5. The method of determining the presence of decay in wood according to claim 1 wherein the wood sample is taken from cut timber.

6. The method of determining the presence of decay in wood according to claim 1 wherein the wood sample is taken from heartwood.

7. The method of determining the presence of decay in wood according to claim 1 wherein the wood sample is taken from sapwood.

8. The method of determining the presence of decay in wood according to claim 1 wherein the ion drift time signature is taken within a time of about 0.3 to 4.5 seconds from entry of the analytes into the ionizing chamber.

9. The method of determining the presence of decay in wood according to claim 1 wherein the ion drift time signature is produced within the time of about 0.3 to 5 seconds from commencement of heating the wood sample.

10. The method of determining the presence of decay in wood according to claim 2 wherein a negative polarity is maintained in the ion mobility spectrometer detector.

11. The method of determining the presence of decay in wood according to claim 2 wherein the wood sample is taken from standing timber.

12. The method of determining the presence of decay in wood according to claim 2 wherein the wood sample is taken from cut timber.

13. The method of determining the presence of decay in wood according to claim 2 wherein the wood sample is taken from heartwood.

14. The method of determining the presence of decay in wood according to claim 2 wherein the wood sample is taken from sapwood.

15. The method of determining the presence of decay in wood according to claim 2 wherein the ion drift time signature is taken within a time of about 0.3 to 4.5 seconds from entry of the analytes into the ionizing chamber.

16. The method of determining the presence of decay in wood according to claim 2 wherein the ion drift time signature is produced within the time of about 0.3 to 5 seconds from commencement of heating the wood sample.

17. A method of determining the presence of decay in a known species of wood, comprising the steps of:
heating at least a portion of a wood sample at a temperature in the range of about 220° to 350° C. to evaporate analytes from the wood sample,
conveying the analytes in a sample gas flow into an ionizing chamber of an ion mobility spectrometer detector,
ionizing the analytes in the ionizing chamber at a temperature in the range of about 220° to 350° C.,
pulsing ions from the ionizing chamber through a gate means into a drift region,
measuring a time of arrival of ions and the ion flux for each pulse with a collector electrode located at the end of the drift region to produce a ionic signal,
amplifying and averaging the ionic signal to generate an ion drift time signature of the sample having peak patterns at different ion drift times, and
comparing the signature of the sample with said known species of wood having decay therein within peak patterns representing decay in said known species of wood, to determine presence of decay in the wood sample.

18. The method of determining the presence of decay in wood according to claim 17 wherein the drift region has a negative polarity.

19. An apparatus for determining presence of decay in a known species of wood, comprising:
means for heating at least a portion of a wood sample at a temperature in the range of about 220° to 350° C. to evaporate analytes from the wood sample,
an ion mobility spectrometer detector adapted to generate an ion drift time signature from the analytes admitted into an ionizing chamber of the detector, the chamber having a temperature in the range of about 220° to 350° C.,
means for transferring analytes from the heating means to the ionizing chamber, and
computing means for comparing peak patterns on the ion drift time signature of the sample with known peak patterns representing decay in said known species of wood, to determine presence of decay in the wood sample.

20. The apparatus for determining presence of decay in wood according to claim 19 wherein the ionizing chamber has a negative polarity.

* * * * *